United States Patent [19]

Rieke et al.

[11] Patent Number: 4,687,489

[45] Date of Patent: Aug. 18, 1987

[54] STABILIZER FOR BIOLOGICAL STAINING SOLUTIONS

[75] Inventors: Erwin Rieke, Seeheim; Renate Kaschek, Reinheim, both of Fed. Rep. of Germany

[73] Assignee: Merck Patent Gesellschaft mit beschrankter Haftung, Darmstadt, Fed. Rep. of Germany

[21] Appl. No.: 909,643

[22] Filed: Sep. 22, 1986

[30] Foreign Application Priority Data

Sep. 20, 1985 [DE] Fed. Rep. of Germany ....... 3533515

[51] Int. Cl.⁴ .......................... G01N 1/30; C09B 67/18; C12M 1/34
[52] U.S. Cl. ............................................ 8/506; 8/606; 8/638; 8/648; 8/655; 8/673; 8/688; 424/3; 424/7.1
[58] Field of Search ................... 8/506, 606, 638, 655; 424/3

[56] References Cited

U.S. PATENT DOCUMENTS

| | | |
|---|---|---|
| 4,290,769 | 9/1981 | Liao et al. ................................ 8/602 |
| 4,363,632 | 12/1982 | Custard et al. .......................... 8/506 |
| 4,382,075 | 5/1983 | Liao et al. ................................ 424/3 |
| 4,392,864 | 7/1983 | Helfrich et al. ......................... 8/506 |
| 4,595,524 | 6/1986 | Yip et al. ........................... 252/408.1 |
| 4,595,582 | 6/1986 | Balogh et al. ........................... 424/3 |

FOREIGN PATENT DOCUMENTS

| | | |
|---|---|---|
| 0049833 | 4/1982 | European Pat. Off. . |
| 0063293 | 10/1982 | European Pat. Off. . |
| 0083027 | 7/1983 | European Pat. Off. . |
| 2516919 | 10/1976 | Fed. Rep. of Germany . |
| 54-89060 | 7/1979 | Japan . |

OTHER PUBLICATIONS

E. Gurr et al., in Venkataraman's "The Chemistry of Synthetic Dyes", vol. VII, (Academic Press, 1974), pp. 278–280, 287–288.

Primary Examiner—A. Lionel Clingman
Attorney, Agent, or Firm—Millen & White

[57] ABSTRACT

Stabilized staining solutions containing dyestuffs and stabilizers, which contain dimethylammonium sulfate as a stabilizer.

20 Claims, No Drawings

STABILIZER FOR BIOLOGICAL STAINING SOLUTIONS

BACKGROUND OF THE INVENTION

This invention relates to stabilizing blood-staining solutions which contain thiazine dyestuffs.

Differential blood stains have long been produced with the known staining solutions of Giemsa, May-Gruenwald, Leishman and Wright. A significant disadvantage of these staining solutions is that analytical results from different laboratories cannot be compared with one another owing to the variable quality of commercially available dyestuffs (J. Clin. Path. 28, 680 (1975)). Not only do large quality differences exist between dyestuffs of different manufacturers, but the dyestuffs are also subject to a chemical change with time. The staining solutions mentioned, owing to the lability in particular of the methylene blue molecule, which, in particular in an alkaline medium, degrades by oxidative demethylation into the next lower homolgues, i.e. azure A, azure B, azure C and thionine, cannot consistently be prepared in the same quality and therefore cannot be standardized either. The low stability of the solutions then gives rise to the formation of precipitations which simultaneously reduces the staining power of the solutions. In essence, the staining properties change due to a decrease in the optical density of the thiazine components, which is determined at about 645 nm. As a result, the blue/red color ratio undergoes a continuous shift, which after some time leads to stainings which are no longer acceptable. It is thus impossible to perform a standardization which, owing to increasing automation, is indispensable in this field.

Attempts have been made, then, to add stabilizers to the staining solutions to obtain reproducible staining power and constant color absorption and also to suppress precipitation. Additives which act as stabilizers are known from EP No. 49,833, EP No. 63,293 and EP No. 83,027. The stabilizing agents used therein are ammonium halides, primary, secondary or tertiary alkylamine hydrohalides or mixtures thereof. In these agents the halide is chloride, bromide or iodide. Hitherto, a preferred stabilizer has been diethylamine hydrochloride.

SUMMARY OF THE INVENTION

It is an object of this invention to provide stabilizers for use in staining solutions which impart a longer stability to the solutions than was attainable by the stabilizers of the prior art.

It is another object of this invention to provide a stabilizer for staining solutions which can be effectively used in low concentrations.

Another object of this invention is to provide a stabilized staining solution which is still usable after prolonged periods of storage.

Upon further study of the specification and appended claims, further objects and advantages of this invention will become apparent to those skilled in the art.

The objects of this invention are attained by providing staining solutions containing dyestuffs and stabilizers, in particular those which contain thiazine dyestuffs or mixtures of thiazine dyestuffs with further dyestuffs, which are characterized in that dimethylammonium sulfate is present as a stabilizer. Dimethylammonium sulfate can be used as the sole stabilizer or in conjunction with other staining solution stabilizers. Such staining solutions, stabilized according to the invention, find utility for staining biological materials in hematology, cytology and histology.

It has been found that by the addition of dimethylammonium sulfate, the stability of a staining solution is much increased compared to the stabilized solutions of the prior art. This finding was all the more surprising in view of the disclosure in EP No. 49,833 which ruled out dimethylammonium chloride as a stabilizer. Dimethylammonium chloride when used as a stabilizer was said to have the big disadvantage of a strong precipitation tendency (cf. J. C. Liao et al., Stain Technology Vol. 56, 251, 1981). In the case of the solutions according to this invention, which contain dimethylammonium sulfate as the stabilizer, no precipitates whatsoever have been observed.

According to this invention a pure thiazine dyestuff solution can be satisfactorily stabilized by adding dimethylammonium sulfate. For instance, the extinction of a 0.1% strength azure B solution at 40° C. decreases by 10% in the course of 2 weeks. However, when 0.2% of dimethylammonium sulfate is added to such a solution, a decrease of only 2% is recorded. It was further found, surprisingly, that the addition of the stabilizer improves the staining properties of the staining solution. The staining properties are improved to such an extent that a significantly lower dyestuff concentration is sufficient for obtaining the usual staining result. For instance, in the preparation of a Wright eosine/methylene blue solution 20% less of the dyestuff can be used when dimethylammonium sulfate is employed as a stabilizer.

The total stabilizer content in the staining solution is as a rule, about 0.05 to 1.5% by weight, relative to the total solution, preferably 0.1 to 0.6% by weight, in particular about 0.2% by weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLES

1. Preparation of a stabilized May-Gruenwald eosine/methylene blue solution 0.1 g of dimethylammonium sulfate is dissolved in 100 ml of methanol. The solution is brought to pH 6.7-7 and; 0.12 g of May-Gruenwald eosine/methylene blue (from Merck) is then added. This is followed by stirring for one hour. The solution is then filtered.

The stability of the staining solutions according to the invention was tested in the following experiments.

In the following comparative experiment (Example 2), a sample of a freshly mixed May-Gruenwald eosine/methylene blue solution was prepared without stabilizer, a second sample of the solution had added to it the hitherto most active stabilizer diethylammonium chloride, and a third sample of the solution had added to it the stabilizer according to the invention, namely dimethylammonium sulfate. The decrease in staining power was determined by the ratio of the optical density at 645 nm to that at 523 nm.

2. Comparative experiments into the stability of differently stabilized solutions The storage behavior (up to 40° C.) of several samples of May-Gruenwald eosine/methylene blue solutions freshly made-up as in Example 1 with each sample containing different stabilizers (See Table 1) was assessed in terms of staining power (i.e., by the ratio of the optical density (OD) 645 nm/523 nm).

TABLE 1

| Time Weeks | Without additive | OD 645 nm/523 nm 0.6% of diethyl-ammonium chloride | 0.1% of dimethyl-ammonium sulfate |
|---|---|---|---|
| 0 | 1.5 | 1.5 | 1.5 |
| 8 | 1.35 | 1.4 | 1.46 |
| 16 | 1.15 | 1.27 | 1.44 |
| 24 | 1.07 | 1.07 | 1.39 |
| 36 | 1.0 | 1.02 | 1.39 |
| 52 | 0.98 | 1.0 | 1.39 |

The decrease in staining power in the sample which contained 0.6% by weight of diethylammonium chloride as a stabilizer was 15.4%, relative to the starting value, after only 16 weeks. After 24 weeks a decrease to 71.3% of the original value was observed and after 52 weeks to 66.7%. Hence, the solution had become practically unusable.

Samples were also prepared using dimethylammonium chloride as a stabilizer, however, these samples showed that dimethylammonium chloride is a completely unsuitable stabilizer since dyestuff precipitates occur.

By comparison, the sample which contained dimethylammonium sulfate as a stabilizer experienced a significantly smaller decrease in staining power, namely only 4% after 16 weeks and 7.4% after 24 weeks.

On even more prolonged storage of 36 to 52 weeks, staining solutions stabilized with dimethylammonium sulfate exhibit no further decrease in staining power, so that even after one year or more it is possible to obtain highly satisfactory and reproducible results with these solutions.

In addition, to obtain this excellent stability of the staining solution of this invention, only 1/6 of the concentration of dimethylammonium sulfate is necessary in comparison to the concentration of diethylammonium chloride used. This activity at very low concentrations, in and of itself, amounts to a significant improvement.

Thus, by means of the above experiments it has been found that on prolonged storage the staining solutions without stabilizer, containing the customary stabilizer diethylammonium chloride or containing dimethylammonium chloride become completely unusable, while solutions containing dimethylammonium sulfate according to the invention still have highly satisfactory values after 52 weeks. Thus, this invention provides new stabilized staining solutions which are very stable in comparison to the stabilized solutions of the prior art.

In the following comparative experiment (Examples 3-5), the stability of staining solutions containing dimethylammonium sulfate as a stabilizer is compared to similar staining solutions containing no stablizer. Stability of the solutions is assessed in terms of staining power, i.e., by the ratio of the optical density (OD) 645 nm/523 nm.

3. Prepartion of a Leishman eosine/methylene blue solution stabilized according to the invention 0.2 g of dimethylammonium sulfate is dissolved in 100 ml of methanol. The solution is brought to pH 6.7-7 and 0.12 g of Leishman's eosine/methylene blue (from Merck) is then added. This is followed by stirring for 18 hours and filtration of the solution.

(Comparative experiment, see Table 2)

4. Preparation of a staining solution with azure B and eosine 0.2 g of dimethylammonium sulfate is dissolved in 100 ml of methanol. The solution is brought to pH 6.7-7 and 0.1 g of azure B (from Merck) and 0.12 g of eosine (from Merck) are added. This is followed by stirring for 24 hours and filtration of the solution.

(Measured values, see Table 2)

5. Preparation of a Wright eosine/methylene blue solution 0.2 g of dimethylammonium sulfate is dissolved in 100 ml of methanol. The solution is brought to pH 6.7-7 and 0.24 g of Wright's eosine/methylene blue (from Merck) is added. This is followed by 18 hours of stirring. The solution is then filtered.

(Measured data, see Table 2)

6. Measured data for different staining solutions with dimethylammonium sulfate as stabilizer.

Table 2 lists measured data (ratios of optical densities) in relation to the storage behavior of different staining solutions stabilized with dimethylammonium sulfate in comparison to staining solutions without any stabilizers.

TABLE 2

| | Staining solutions | | | | | | | |
|---|---|---|---|---|---|---|---|---|
| | Wright OD 646 nm/523 nm | | Azure B/eosine OD 637 nm/523 nm | | Leishman OD 625 nm/523 nm | | May-Grunwald OD 645 nm/523 nm | |
| Time weeks | Without additive | 0.2% of di-methylammonium sulfate | Without additive | 0.2% of di-methylammonium sulfate | Without additive | 0.2% of di-methylammonium sulfate | Without additive | 0.1% of di-methylammonium sulfate |
| 0 | 1.62 | 1.62 | 1.40 | 1.40 | 1.34 | 1.34 | 1.5 | 1.5 |
| 8 | 1.49 | 1.61 | | | 1.26 | 1.34 | 1.35 | 1.46 |
| 16 | | | 1.25 | 1.38 | | | 1.15 | 1.44 |
| 24 | 1.39 | 1.61 | 1.0 | 1.36 | 1.23 | 1.34 | 1.07 | 1.39 |
| 52 | 0.84 | 1.42 | 0.77 | 1.32 | 0.97 | 1.26 | 0.98 | 1.39 |

With all the staining solutions stabilized with dimethylammonium sulfate, staining after 1 year is still very good, and reproducible results are obtainable. Analogous results are obtained on adding, for example, 0.6 g or 1.5 g of dimethylammonium sulfate to the corresponding solutions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a staining solution for biological materials containing at least one thiazine dyestuff and at least one stabilizer, the improvement wherein the stabilizer is dimethylammonium sulfate.

2. A staining solution according to claim 1, wherein the concentration of said stabilizer is 0.05 to 1.5% by weight.

3. A staining solution according to claim 1, wherein the concentration of said stabilizer is 0.05 to 1.5% by weight.

4. A staining solution according to claim 2, wherein the concentration of said stabilizer is 0.1 to 0.6% by weight.

5. A staining solution according to claim 3, wherein the concentration of said stabilizer is 0.1 to 0.6% by weight.

6. A staining solution according to claim 4, wherein the concentration of said stabilizer is about 0.2 by weight.

7. A staining solution according to claim 5, wherein the concentration of said stabilizer is about 0.2 by weight.

8. A method of stabilizing a staining solution comprising adding to said solution an amount of dimethylammonium sulfate effective to stabilize said solution.

9. A method of preparing a specimen for hematology comprising staining the specimen with a solution according to claim 1.

10. A method of preparing a specimen for cytology comprising staining the specimen with a solution according to claim 1.

11. A method of preparing a specimen for histology comprising staining the specimen with a solution according to claim 1.

12. A staining solution according to claim 1, wherein the dyestuff is eosine.

13. A staining solution according to claim 1, wherin the dyestuff is methylene blue.

14. A staining solution according to claim 1, wherein the dyestuff is azure B.

15. A staining solution according to claim 1, wherein the dyestuff is a mixture of eosine and methylene blue.

16. A staining solution according to claim 1, wherein the dyestuff is a mixture of eosine and azure B.

17. A staining solution according to claim 1, wherein said solution is a Giemsa solution.

18. A staining solution according to claim 1, wherein said solution is a May-Gruenwald solution.

19. A staining solution according to claim 1, wherein said solution is a Leishman solution.

20. A staining solution according to claim 1, wherien said solution is a Wright solution.

* * * * *